United States Patent [19]

Eichenberger et al.

[11] 4,029,795

[45] June 14, 1977

[54] 4(2' ISOQUINOLIN-1-ONE)PIPERIDINES

[75] Inventors: Kurt Eichenberger, Therwil; Christian Egli, Magden; Hans Kühnis, Basel; Oswald Schier, Oberwil, all of Switzerland

[73] Assignee: Ciba-Geigy Corporation, Ardsley, N.Y.

[22] Filed: July 14, 1975

[21] Appl. No.: 595,456

[30] Foreign Application Priority Data

July 31, 1974 Switzerland .................... 10583/74

[52] U.S. Cl. .......................... 424/258; 260/286 R; 260/287 K; 260/288 D; 260/289 K; 260/293.88

[51] Int. Cl.² ................ A61K 31/47; C07D 217/00

[58] Field of Search ....... 260/287 K, 289 K, 288 D, 260/286 R, 286 D; 424/258

[56] References Cited

UNITED STATES PATENTS

| | | | |
|---|---|---|---|
| 3,594,380 | 7/1971 | Sulkowski | 424/258 |
| 3,600,394 | 8/1971 | Coyne | 424/258 |
| 3,753,994 | 8/1973 | Diana | 424/258 |
| 3,879,553 | 4/1975 | Tobol | 424/258 |

*Primary Examiner*—Donald G. Daus
*Assistant Examiner*—David E. Wheeler
*Attorney, Agent, or Firm*—Joseph G. Kolodny; John J. Maitner; Theodore O. Groeger

[57] ABSTRACT

1-(3-Aryloxy-2-hydroxypropyl)-4-(1-oxoisoquinolino)-piperidines, e.g. those of the formula R'=H, alkanoylaminoethenyl, carbamoyl, alkanoyl, CN, alkoxycarbonylamino-lower alkyl, halo, OH, alkanoylamino, alkyl, alkoxy, alkenyl, alkenyloxy
R''=H, alkyl, alkoxy, alkenyl, alkenyloxy,
R'''= alkanoylamino, $NH_2$, $NO_2$, alkyl, alkoxy, halo $CF_3$, OH 2-alkanoic acid esters and acid addition salts thereof are antihypertensive and antiarrhythmic agents.

9 Claims, No Drawings

4(2' ISOQUINOLIN-1-ONE)PIPERIDINES

SUMMARY OF THE INVENTION

The invention relates to new piperidines of the formula

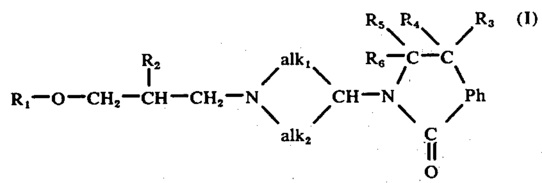

wherein $R_1$ denotes an optionally substituted aryl radical, $alk_1$ and $alk_2$ independently of one another are lower alkylene radicals which each separate the nitrogen atom bonded to them, and the methine group bonded to them, by 2 carbon atoms, $R_2$ denotes an optionally acylated hydroxyl group, Ph denotes an optionally substituted o-phenylene radical, $R_3$ denotes a hydrogen atom, a lower alkyl radical or the hydroxyl group and $R_5$ denotes a lower alkyl radical or a hydrogen atom or $R_3$ and $R_5$ together represent a second bond and $R_4$ and $R_6$ each denote a hydrogen atom, or $R_4$ together with $R_3$ represents an oxo group, $R_5$ denotes a lower alkyl radical or a hydrogen atom and $R_6$ denotes a hydrogen atom, or $R_6$ together with $R_5$ represents an oxo group, $R_3$ denotes a hydrogen atom, a lower alkyl radical or the hydroxyl group and $R_4$ represents a hydrogen atom, and their salts, as well as processes for the manufacture and application of these products, which are useful antihypertensive, vasodilating, antiarrhythmic, noradrenolytic and positively inotropic agents.

DESCRIPTION OF THE PREFERRED EMBODIMENTS

An optionally substituted aryl radical $R_1$ is, for example, a phenyl or naphthyl radical substituted by one, two or more substituents and also, for example, an optionally substituted 5,6,7,8-tetrahydro-1- or -2-naphthyl radical. A monosubstituted or disubstituted phenyl radical or naphthyl radical is preferred, and a monosubstituted phenyl radical is preferred very particularly.

The aryl radical $R_1$ is, for example, substituted by aliphatic hydrocarbon radicals, especially by lower aliphatic hydrocarbon radials which can also be substituted. Examples of such optionally substituted lower aliphatic hydrocarbon radicals are lower alkyl groups, lower alkenyl groups, lower alkinyl groups, lower alkoxy-lower alkyl groups, lower alkylthio-lower alkyl groups, hydroxy-lower alkyl groups, halogeno-lower alkyl groups, lower alkoxycarbonylamino-lower alkyl groups and acylamino-ethenyl groups.

A substituent of an aryl radical $R_1$ can also be hydroxyl which is optionally etherified by an aliphatic hydrocarbon radical, especially by a lower aliphatic hydrocarbon radical, which can be substituted yet further. Examples of such radicals are lower alkoxy groups, lower alkenyloxy groups, lower alkinyloxy groups, hydroxy-lower alkoxy groups, lower alkoxy-lower alkoxy groups, lower alkylthio-lower alkoxy groups, aryl-lower alkoxy groups, such as phenyl-lower alkoxy groups, and hydroxyl groups.

The aryl radical $R_1$ can also be substituted by the following substituents: lower alkanoyl groups, lower alkanoyloxy groups, lower alkylmercapto groups, acylamino groups, halogen atoms or nitrile, amino and nitro groups.

Further possible substituents of the aryl radical $R_1$ are optionally substituted carbamoyl groups, such as, for example, N-mono-lower alkylcarbamoyl groups, N,N-di-lower alkylcarbamoyl groups of N,N-lower alkylencarbamoyl groups.

Further possible substituents of the aryl radical $R_1$ are optionally substituted ureido groups.

Substituents of the aryl radical which should be singled out particularly are optionally lower-alkylated carbamoyl radicals, acylaminoethenyl radicals, such as, for example, lower alkanoylaminoethenyl radicals and lower alkoxycarbonylamino-lower alkyl radicals (which are preferably in the para-position on the phenyl radical), as well as nitrile groups (which are preferably in the ortho-position on the phenyl radical) and lower alkanoyl radicals (which are preferably in the ortho- or para-position on the phenyl radical). However, particularly preferred substituents of the aryl radical are halogen atoms (which are preferably in the o-position on the phenyl radical), and hydroxyl groups (which are preferably in the para-position on the phenyl radical) and above all lower alkoxy-lower alkyl groups and acylamino groups (which are preferably in the para-position on the phenyl), as well as lower alkyl radicals, lower alkenyl radicals, lower alkoxy groups and lower alkenyloxy groups (which are preferably in the ortho-position on the phenyl).

Examples of lower alkylene radicals $alk_1$ and $alk_2$ are 2,3-butylene radicals, 1,2-butylene radicals or preferably 1,2-propylene radicals or especially 1,2-ethylene radicals.

The o-phenylene radical Ph can carry one, two or more substituents; however, it preferably does not contain more than two substituents. Possible substituents of the o-phenylene radical are, in particular: lower alkyl radicals, lower alkoxy groups, halogen atoms, trifluoromethyl groups, hydroxyl groups and, as a second choice, also acylamino groups, nitro groups and amino groups.

An optionally acylated hydroxyl group $R_2$ is, for example, a lower alkanoyloxy group, such as, for example, an acetoxy, propionyloxy or butyryloxy group or preferably the pivaloyloxy group, or above all a free hydroxyl group.

Where not stated otherwise, lower radicals are those radicals which contain not more than 7 carbon atoms and preferably up to 4 carbon atoms.

Examples of lower alkyl radicals are methyl, ethyl, n-propyl or ispropyl radicals, or straight-chain or branched butyl, pentyl or hexyl radicals which can be bonded in any desired position.

Lower alkenyl radicals are, in particular, allyl or methallyl radicals and a possible alkinyl radical is above all the propargyl radical.

Lower alkoxy-lower alkyl radicals are, for example, those composed of the lower alkyl radicals mentioned, for example methoxymethyl, ethoxymethyl, n-propoxymethyl, n-butoxymethyl, 2-(n-butoxy)-ethyl, 3-(n-propoxy)-propyl or especially 2-methoxyethyl.

Lower alkylthio-lower alkyl groups are, for example, those composed of the lower alkyl radicals mentioned and are thus, for example, methylthiomethyl, 2-ethylthioethyl, 3-methylthio-n-propyl and especially 2-methylthioethyl.

Hydroxy-lower alkyl groups are above all those in which the lower alkyl part has the above meaning, such as, for example, 2-hydroxyethyl, 3-hydroxy-n-propyl and especially hydroxymethyl.

Possible halogeno-lower alkyl radicals are especially those which are derived from the alkyl radicals mentioned and in which the halogen atom is a bromine atom or especially a chlorine atom or fluorine atom, such as, for example, chloromethyl, 2-chloroethyl, dichloromethyl and especially trifluoromethyl.

Lower alkoxycarbonylamino-lower alkyl groups are understood, for example, as those radicals of which the lower alkyl parts are derived from the lower alkyl groups mentioned. Such groups are, for example, methoxycarbonylaminomethyl, ethoxycarbonylaminomethyl, 4-methoxycarbonylamino-n-butyl, 2-ethoxycarbonylaminoethyl, 3-ethoxycarbonylamino-n-propyl and especially 2-methoxycarbonylamino-ethyl and 3-methoxycarbonylamino-n-propyl.

Acylamino-ethenyl groups are in particular radicals of the formula

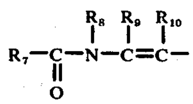

wherein $R_7$ is a lower alkyl or lower alkoxy group, for example one of those mentioned above or below, or an amino group, that is to say a primary, secondary or tertiary amino group, preferably a mono- or di-lower alkylamino group, wherein possible lower alkyl radicals are those mentioned; $R_8$ is hydrogen or a lower alkyl group, for example one of those mentioned; $R_9$ is hydrogen, a lower alkyl group, for example one of those mentioned, carboxyl or lower alkoxycarbonyl, wherein the lower alkoxy part is derived, for example, from the lower alkyl radicals mentioned; $R_{10}$ is hydrogen or a lower alkyl group, for example one of those mentioned.

Lower alkoxy radicals are especially those radicals which are derived from the lower alkyl radicals mentioned. Examples of such lower alkoxy radicals are methoxy, ethoxy, n-propoxy, isopropoxy, n-butoxy and n-amyloxy. To lower alkoxy radicals, especially two adjacent lower alkoxy radicals, can also be linked, as in the case of lower alkylenedioxy, for example methylenedioxy.

Examples of lower alkenyloxy radicals are allyloxy or methallyloxy radicals.

Lower alkinyloxy radicals are in particular propargyloxy radicals.

Hydroxy-lower alkoxy radicals are especially those derived from the hydroxy-lower alkyl groups mentioned but wherein preferably the 2 oxygen atoms are separated by at least 2 carbon atoms.

Lower alkoxy-lower alkoxy radicals are, for example, those derived from the lower alkoxy radicals mentioned. Examples of such radicals are methoxymethoxy, ethoxymethoxy, 1-methoxyethoxy, 4-methoxy-n-butoxy, 3-methoxy-n-butoxy and especially 3-methoxy-n-propoxy, 2-methoxyethoxy and 2-ethoxyethoxy.

Lower alkylthio-lower alkoxy groups are, for example, those groups which are derived from the lower alkyl radicals mentioned. Examples of such groups are methylthiomethoxy, 2-ethylthioethoxy, 3-methylthio-n-propoxy and especially 2-methylthioethoxy.

Phenyl-lower alkoxy radicals are especially α-phenyl-lower alkoxy radicals, such as benzyloxy radicals, but can also be other radicals of this type which are derived from the lower alkyl radicals mentioned, such as, for example, the phenethoxy radical.

Lower alkanoyl radicals to be mentioned are above all pivaloyl, propionyl or butyryl radicals, but above all the acetyl radical; examples of alkanoyloxy radicals are those in which the alkanoyl part has the above meaning.

Examples of lower alkylmercapto groups are those groups derived from the lower alkyl radicals mentioned. Examples of such groups are ethylmercapto, isopropylmercapto, n-butylmercapto and especially methylmercapto.

Acylamino groups are especially those which contain cycloaliphatic, aromatic, araliphatic and above all aliphatic acyl radicals as the acyl radicals.

Aliphatic acyl radicals of the formula R—CO— are especially those in which R is a lower alkyl radical, for example one of those mentioned.

Cycloaliphatic acyl radicals of the formula R′—CO— are especially those in which R′ denotes an optionally lower alkylated lower cycloalkyl radical, above all with 3–7, especially 5–7, ring members, such as, for example, the cyclopropyl, cyclopentyl, cyclohexyl or cycloheptyl radical.

Examples of aromatic or araliphatic acyl radicals which may be mentioned are benzoyl and naphthoyl radicals and phenyl-lower alkanoyl radicals, such as phenylacetyl and α- and β-phenylpropionyl radicals.

The acyl radicals mentioned can be substituted yet further.

The following may be mentioned as substituents of the aromatic and araliphatic acyl radicals, the substituents preferably being present in the rings: lower alkyl or alkoxy radicals, such as those mentioned above, halogen atoms, such as those mentioned below, or the pseudohalogen trifluoromethyl. The radicals can be monosubstituted, disubstituted or polysubstituted.

Preferred acyl radicals are benzoyl and particularly lower alkanoyl, such as acetyl.

Possible halogen atoms are especially fluorine or bromine atoms, but particularly chlorine atoms.

The N-mono-lower alkylcarbamoyl and N,N-di-lower alkylcarbamoyl groups for example contain, as the lower alkyl part, the abovementioned lower alkyl radicals. The N,N-lower alkylenecarbamoyl radicals contain, as lower alkylene radicals, especially butylene-1,4 or pentylene-1,5 radicals. Examples of such radicals are N-methylcarbamoyl, N,N-dimethylcarbamoyl, pyrrolidino-carbocarbonyl and piperidino-carbonyl radicals.

An optionally substituted ureido group is, for example a ureido group in which the free amino group can optionally be substituted by lower alkyl groups, for example those mentioned, such as, for example, a N′,N′-dimethylureido group or N′,N′-diethylureido group, If the ureido group is substituted by divalent radicals, then these are radicals which can optionally be interrupted by hetero-atoms and/or be substituted, preferably lower alkylene radicals, which can be straight-chain or branched and above all have 4–6 chain carbon atoms if the carbon chain is uninterrupted or 4 to 5 carbon atoms if the carbon chain is interrupted by hetero-atoms. Possible hetero-atoms are, in particular, oxygen, sulphur and nitrogen. Examples of such radicals are butylene-(1,4), pentylene-(1,5), hexylene-(1,5), hexylene-(2,5), hexylene-(1,6), heptylene-(1,6)

3-oxapentylene-(1,5), 3-oxahexylene-(1,6), 3-thia-pentylene-(1,5), 2,4-dimethyl-3-thia-pentylene-(1,5) and 3-lower alkyl-3-aza-pentylene-(1,5) radicals, such as 3-methyl-3-aza-pentylene-(1,5) or 3-aza-hexylene-(1,6) radicals.

The new compounds possess valuable pharmacological properties. Thus they show a blood pressure-lowering action, as can be demonstrated in animal experiments, for example on intravenous administration of doses of about 0.01–1 mg/kg to narcotised cats. Furthermore, the new compounds cause an inhibition of tachycardia, as can also be shown in animal experiments, for example in in vitro experiments at concentrations of 0.3–3 γ/ml on an isolated guinea-pig heart by the Langendorff method (resolution of the tachycardia by isoproterenol [$5 \times 10^{-9}$ γ/ml] or histamine [$3 \times 10^{-7}$ γ/ml). Furthermore, the new compounds cause a vasodilatation which can be demonstrated on aminals, for example on narcotised dogs, by measuring the haemodynamics on intraduodenal administration in a dose of about 10 mg/kg.

The new compounds further possess a noradrenolytic action which can be demonstrated in vitro, for example in experiments on isolated perfused mesenteric arteries of rats at concentrations of 0.001–0.01 γ/ml.

The new compounds further shown an anti-arrythmic and positively inotropic effect.

Accordingly, the new compounds can in particular be used as anti-hypertensive agents and as vasodilatant agents. Further, the new compounds can serve as starting materials or intermediate products for the manufacture of other compounds, especially pharmaceutically active compounds.

Compounds to be mentioned particularly are those of the formula

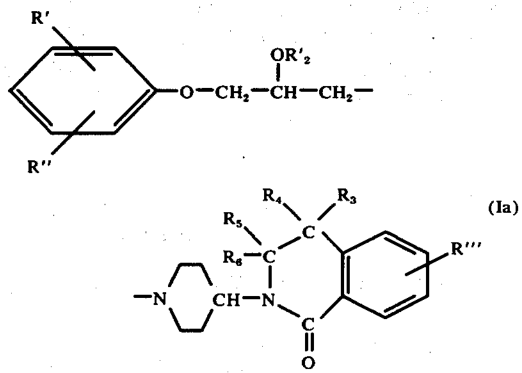

wherein R'- denotes a hydrogen atom, a p-alkanoylaminoethenyl radicals, an optionally lower alkylated p-carbamoyl radical, an o- or p-lower alkanoyl radical, and o-nitrile group, a p-lower alkoxycarbonylamino-lower alkyl radical, an o-halogen atom or a p-hydroxyl group or above all a p-lower alkanoylamino radical, a p-[2(lower alkoxy)ethyl] radical, a lower o-alkyl or o-alkoxy radical, or an o-alkenyl or o-alkenyloxy radical, R'' denotes a lower alkyl radical, a lower alkoxy radical, a lower alkenyl radical, a lower alkenyloxy radical or above all a hydrogen atom, $R'_2$ denotes a lower alkanoyl radical, such as, in particular, the acetyl, propionyl or pivalyl radical, or above all a hydrogen atom, $R_3$ denotes a hydrogen atom or the hydroxyl group and $R_5$ denotes a hydrogen atom, or $R_3$ and $R_5$ together represent a second bond and $R_4$ and $R_6$ each denote a hydrogen atom, or $R_4$ together with $R_3$ represents an oxo group and $R_5$ and $R_6$ each denote a hydrogen atom, or $R_6$ together with $R_5$ represents an oxo group and $R_3$ and $R_4$ each denote a hydrogen atom and R''' denotes a lower alkanoylamino radical, the amino group, the nitro group or, above all, a lower alkyl radical, a lower alkoxy group, a halogen atom, the trifluoromethyl radical or the hydroxyl group, and their salts.

Compounds to be mentioned especially are in particular those of the formula Ia, wherein R' denotes a p-lower alkanoylamino radical, for example p-acetylamino, a p-[2-(lower alkoxy)-ethyl] radical, for example 2-methoxyethyl, or especially a lower o-alkenyl or o-alkenyloxy radical, for example o-allyl or o-allyloxy, or above all a lower o-alkyl or o-alkoxy radical, such as the o-methyl or o-methoxy radical, R'' represents hydrogen, $R_2'$ denotes the acetyl, propionyl or, in particular, pivalyl radical, or above all a hydrogen atom, $R_3$ denotes a hydrogen atom or the hydroxyl group and $R_5$ denotes a hydrogen atom or $R_3$ and $R_5$ together represent a second bond and $R_4$ and $R_6$ each denote a hydrogen atom, or $R_4$ together with $R_3$ represents an oxo group and $R_5$ and $R_6$ each denote a hydrogen atom, or $R_6$ together with $R_5$ represents an oxo group and $R_3$ and $R_4$ each denote a hydrogen atom, but in which above all $R_4$ and $R_6$ each represent hydrogen and $R_3$ and $R_5$ either represent a second bond or each denote a hydrogen atom, and R''' denotes a lower alkyl radical, for example methyl, a lower alkoxy radical, for example methoxy, a halogen atom, for example chlorine, the trifluoromethyl radical or, in particular, a hydrogen atom, and their salts.

Compounds to be mentioned specifically are 2-{1-[3-(o-allyloxy-phenoxy)-2-hydroxypropyl]-4-piperidyl}-3,4-dihydro-1(2H)-isoquinolinone, 2-{1-[3-(o-chlorophenoxy)-2-hydroxypropyl]-4-piperidyl}-3,4-dihydro-1(2H)-isoquinolinone, 2-{1-[3-(o-methoxy-phenoxy)-2-pivaloyloxypropyl]-4-piperidyl}-3,4-dihydro-1(2H)-isoquinolinone, 2-{1-[3-(o-tolyloxy)-2-hydroxypropyl]-4-piperidyl}-3,4-dihydro-1(2H)-isoquinolinone, and above all 2-{1-[3-(o-methoxy-phenoxy)-2-hydroxypropyl]-4-piperidyl}-3,4-dihydro-1(2H)-isoquinolinone which, for example, when administered intravenously, in a dose of about 0.01 mg/kg, to narcotised cats, causes a distinct lowering of the blood pressure.

The new compounds are obtained according to methods which are in themselves known.

For example, a compound of the formula $$R_1 - O - Y_1 \quad (II)$$

can be reacted with a compound of the formula

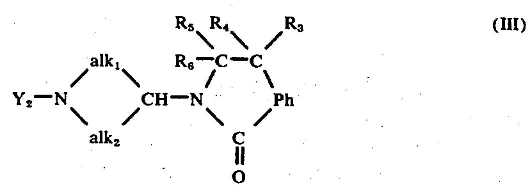

wherein $R_1$, $alk_1$, $alk_2$, Ph, $R_3$, $R_4$, $R_5$ and $R_6$ have the indicated meanings, one of the radicals $Y_1$ and $Y_2$ represents hydrogen and the other denotes a radical of the formula

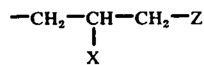

and X represents the group $R_2$, wherein $R_2$ has the indicated meaning, and Z denotes a reactively esterified hydroxyl group, or X and Z together form an epoxy group.

Thus, for example, a possible procedure is to react a compound of the formula

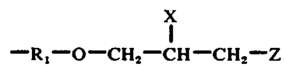

with a compound of the formula

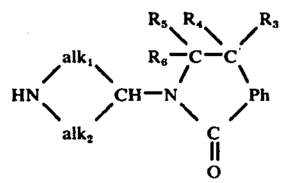

wherein $alk_1$, $alk_2$, Ph, $R_3$, $R_4$, $R_5$ and $R_6$ have the above meanings and either X represents the group $R_2$, wherein $R_2$ has the indicated meanings, and Z represents a reactive esterified hydroxyl group, or X and Z together form an epoxy group.

A reactive esterified hydroxyl group is, in particular, a hydroxyl group esterified by a strong inorganic or organic acid, above all a hydrogen halide acid, such as hydrochloric acid, hydrobromic acid, hydriodic acid or sulphuric acid, or an organic sulphonic acid, for example benzenesulphonic acid, p-bromobenzenesulphonic acid or p-toluenesulphonic acid. Thus, Z in particular represents chlorine, bromine or iodine.

This reaction is carried out in the usual manner. When a reactive ester is used as the starting material, the reaction is preferably carried out in the presence of a basic condensation agent and/or with an excess of the compound of the formula IIIa.

Further, a compound of the formula $$R_1 - OH \quad \text{(IIb)}$$

wherein $R_1$ has the above meanings, can be reacted with a compound of the formula

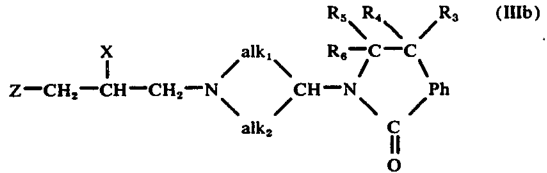

wherein X, Z, $alk_1$, $alk_2$, Ph, $R_3$, $R_4$, $R_5$ and $R_6$ have the above meanings.

This reaction is carried out in the usual manner. If reactive esters are used as the starting material, the compound of the formula IIb can preferably be used in the form of its metal phenolate, such as alkali metal phenolate, for example sodium phenolate, or the reaction is carried out in the presence of an acid-binding agent, especially of a condensation agent, which can form a salt with the compound of the formula IIb, such as an alkali metal alcoholate.

The new compounds in which $R_3$ is hydroxyl can furthermore be manufactured by reducing the oxo group of the propyl chain to a hydroxyl group in a compound of the formula

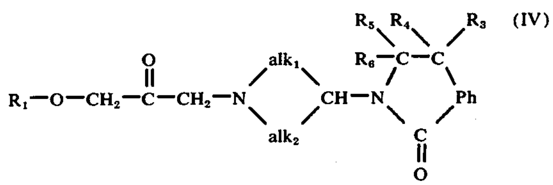

wherein $R_1$, $alk_1$, $alk_2$, Ph, $R_3$, $R_4$, $R_5$ and $R_6$ have the above meanings.

This reduction is carried out in the usual manner, in particular using a di-light metal hydride, such as sodium borohydride. However, the reduction can also be carried out with nascent hydrogen. Nascent hydrogen can be obtained for this purpose by reaction of metals or metal alloys on agents which provide hydrogen, such as carboxylic acid, alcohols or water, and in particular zinc or zinc alloys together with acetic acid, or alkali metals and alcohol, such as sodium and ethanol, can be used.

The reduction can furthermore be carried out by catalytic hydrogenation, such as with hydrogen in the presence of a hydrogenation catalyst, for example heavy metals such as palladium, platinum or Raney nickel. Care must be taken that other reducible groups are not attacked during the reduction.

The new compounds can also be obtained when the pyridinium ring is reduced to the piperidine ring in a compound of the formula

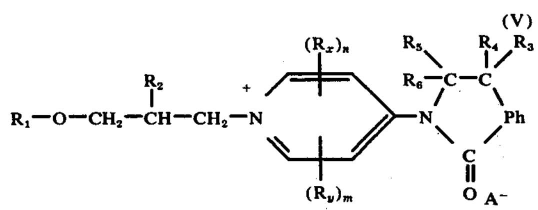

wherein $R_1$, $R_2$, $R_3$, $R_4$, $R_5$, $R_6$ and Ph have the above meanings, $R_x$ and $R_y$ independently of one another denote lower alkyl radicals or hydrogen atoms and $n$ and $m$ represent 1 or 2 and $A^-$ is an anion.

The reduction can be carried out in the usual manner, preferably by catalytic hydrogenation, such as with hydrogen in the presence of a hydrogenation catalyst, for example heavy metals, such as palladium, platinum or Raney nickel, or with nascent hydrogen, such as, for example, is produced by sodium and an alcohol, such as a lower alkanol, for example ethanol.

Care must be taken that other reducible groups are not attacked in the reduction.

The new compounds can also be obtained by intramolecular condensation of a compound of the formula (VI)

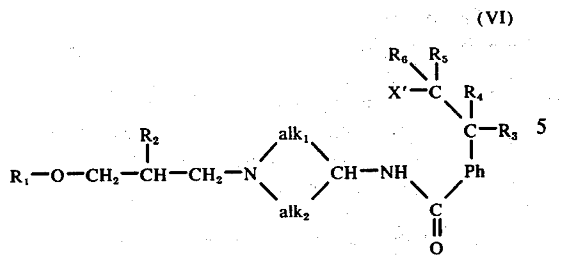

wherein $R_1$, $R_2$, $alk_1$, $alk_2$, Ph, $R_3$, $R_4$, $R_5$ and $R_6$ have the indicated meanings and X' denotes a reactive esterified hydroxyl group.

A reactive esterified hydroxyl group is in particular one of those mentioned above.

The cyclisation (intramolecular condensation) can be carried out in the usual manner, preferably in the presence of a solvent, such as an inert polar solvent, such as an alcohol, for example ethanol or isopropanol, or dimethylformamide, and advantageously in the presence of a condensation agent, particularly of a basic condensation agent. The cyclisation is preferably carried out in the presence of an alkali metal hydroxide, carbonate or bicarbonate or alkaline earth metal hydroxide, carbonate or bicarbonate, for example sodium hydroxide, potassium hydroxide, calcium hydroxide, sodium carbonate, potassium carbonate, calcium carbonate, sodium bicarbonate or potassium bicarbonate, or of an alkali metal acetate, such as sodium acetate, or of an alkali metal alcoholate, such as sodium methylate, or of organic tertiary nitrogen bases, such as trialkylamines, for example trimethylamine or triethylamine, or pyridine.

The new compounds in which $R_3$ and $R_5$ together represent a second bond can also be obtained when a compound of the formula (VII)

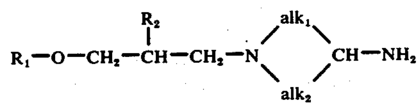

is reacted with a compound of the formula (VIII)

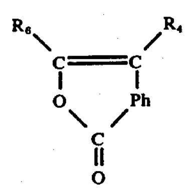

wherein $R_1$, $R_2$, $R_4$, $R_6$, $alk_1$, $alk_2$ and Ph have the indicated meanings.

The reaction can be carried out in a manner which is in itself known. It is advantageously carried out in the presence of an organic base, such as a tertiary amine, above all pyridine, and this base can also simultaneously serve as the solvent. However, the reaction can also be carried out in the presence of further solvents.

The new compounds can also be obtained by intramolecular condensation of a compound of the formula (IX)

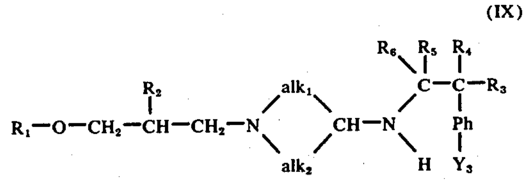

wherein $R_1$, $R_2$, $alk_1$, $alk_2$, $R_3$, $R_4$, $R_5$, $R_6$ and Ph have the indicated meanings, and $Y_3$ denotes a free carboxyl group or preferably a functionally modified carboxyl group which contains an oxo group.

A functionally modified carboxyl group which contains an oxo group is, for example, an esterified carboxyl group such as, in particular, a carboxyl group esterified with a lower alkanol or aralkanol, such as methanol, phenol, p-nitrophenol or benzyl alcohol, or an activated esterified carboxyl group, such as a carboxyl group esterified with cyanomethanol, or an acid halide grouping, such as, in particular, an acid chloride grouping, or an acid azide, acid amide or acid anhydide grouping. Possible acid anhydride groupings are especially those of mixed anhydrides, especially of mixed anhydrides with carbonic acid monoalkyl esters, such as carbonic acid monoethyl ester or carbonic acid monoisobutyl ester.

The reaction can be carried out in the usual manner. Preferably, elevated temperatures are used. The reaction is advantageously carried out in a solvent, such as an inert solvent, for example a hydrocarbon, such as benzene or toluene, or in a high-boiling inert solvent such as, for example, diphenyl ether.

The new compounds in which $R_2$ represents hydrogen, can also be obtained when, in a compound of the formula (X)

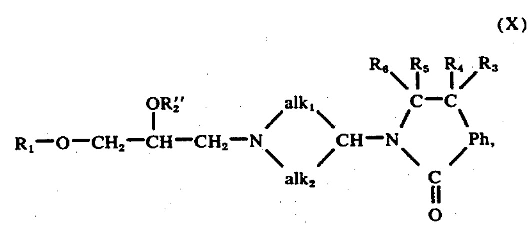

wherein $R_1$, $alk_1$, $alk_2$, Ph, $R_3$, $R_4$, $R_5$ and $R_6$ have the indicated meanings and $R_2''$ denotes a radical which can be split off by hydrogenolysis, $R_2''$ is split off by hydrogenolysis.

A radical which can be split off by hydrogenolysis is above all an $\alpha$-aralkyl radical, such as the benzyl radical, or an $\alpha$-aralkoxycarbonyl radical, such as the carbobenzoxy radical. The hydrogenolysis can be carried out in the usual manner, preferably by means of hydrogen in the presence of a hydrogenation catalyst, such as a nickel, palladium, platinum or ruthenium catalyst.

The new compounds of the formula I, wherein $R_6$ together with $R_5$ forms an oxo group, can also be obtained when a compound of the formula (VII)

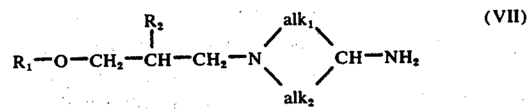

wherein $R_1$, $R_2$ $alk_1$ and $alk_2$ have the above meanings, is reacted with a compound of the formula

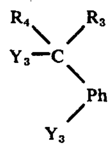

(XI)

wherein $R_3$, $R_4$ and Ph have the above meanings and the substituents $Y_3$ independently of one another represent a free carboxyl group or preferably a functionally modified carboxyl group which contains an oxo group, or together represent the grouping

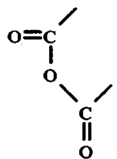

A functionally modified carboxyl group which contains an oxo group is, for example, an esterified carboxyl group such as, in particular, a carboxyl group esterified with a lower alkanol or aralkanol, such as methanol, phenol, p-nitrophenol or benzyl alcohol, or an activated esterified carboxyl group, such as a carboxyl group esterified with cyanomethanol, or an acid halide grouping, such as, in particular, an acid chloride grouping, or an acid azide, acid amide or acid anhydride grouping. Possible acid anhydride groupings are in particular those of mixed anhydrides, especially of mixed anhydrides with carbonic acid monoalkyl esters, such as carbonic acid monoethyl ester or carbonic acid monoisobutyl ester.

The reaction can be carried out in the usual manner. Preferably, elevated temperatures are used. The reaction is advantageously carried out in a solvent, such as an inert solvent, for example a hydrocarbon, such as benzene or toluene, or in a high-boiling inert solvent such as, for example, diphenyl ether.

In resulting compounds, substituents can be split off, introduced or converted, within the scope of the end products.

Thus, for example, in compounds of the formula I, wherein $R_1$ denotes an aryl radical which is substituted by a radical Z″ which can be converted into an optionally substituted carbamoyl group, Z″ can be converted into an optionally substituted carbamoyl group.

A radical Z″ is in this case above all an optionally functionally modified carboxyl group containing an oxo group.

A functionally modified carboxyl group which contains an oxo group is, for example, an esterified carboxyl group, such as, in particular, a carboxyl group esterified with a lower alkanol or aralkanol, such as methanol, phenol, p-nitrophenol or benzyl alcohol, or an activated esterified carboxyl group, such as a carboxyl group esterified with cyanomethanol, or an acid halide grouping, such as, in particular, an acid chloride grouping, or an acid azide grouping or acid anhydride grouping. Possible acid anhydride groupings are in particular those of mixed anhydrides, especially of mixed anhydrides with carbonic acid monoalkyl esters, such as carbonic acid monoethyl ester or carbonic acid monoisobutyl ester.

The conversion of the group Z″ is effected, for example, by reaction with ammonia or with a corresponding amine possessing at least 1 hydrogen atom.

The reaction is carried out in the usual manner, in particular at elevated temperature, if necessary at drastically elevated temperature, such as at a temperature which may even be above 200° C, if desired under pressure and if desired with an excess of the particular amine. If the reaction is carried out at room temperature or only moderately elevated temperature, it is preferably carried out in an inert solvent using a longer reaction time. Examples of inert solvents are alcohols, such as methanol and ethanol, ethers, such as diethyl ether or dioxane, benzene and the like.

Furthermore, for example, in compounds of the formula I, wherein $R_1$ denotes an aryl radical substituted by a radical Z‴ which can be converted into an optionally substituted ureido group. Z‴ can be converted into an optionally substituted ureido group.

Z‴ is here in particular a reactively modified carboxyamino radical, such as a carboxyamino radical esterified by a lower alkanol or phenol, or a corresponding halogenocarbonylamino radical, such as, in particular, a chlorocarbonylamino radical.

The conversion to the ureido group is carried out, for example, by reaction with ammonia or a corresponding amine possessing at least 1 hydrogen atom.

This reaction can be carried out in the usual manner, especially using an excess of ammonia or amine and optionally in a solvent and preferably at elevated temperature.

Furthermore, resulting compounds in which $R_1$ denotes an aryl radical substituted by a hydroxyalkyl, hydroxyalkoxy, mercaptoalkyl or mercaptoalkoxy radical, can be alkylated, for example by reaction with a reactive ester of a corresponding alkanol. Reactive esters are here above all esters with strong inorganic or organic acids, preferably with hydrogen halide acids, such as hydrochloric acid, hydrobromic acid or hydriodic acid, with sulphuric acid or with arylsulphonic acids, such as benzenesulphonic acid, p-bromobenzenesulphonic acid or p-toluenesulphonic acid.

The reaction can be carried out in the usual manner, advantageously in the presence of solvents and, for example, in the presence of condensation agents, such as basic condensation agents, at lowered, ordinary or elevated temperature.

Furthermore, in compounds of the formula I, wherein $R_1$ denotes an aryl radical substituted by a $Z_2$-alkyl or $Z_2$-alkoxy radical and $Z_2$ represents a reactively esterified hydroxyl group, $R_1$ can be converted into alkoxy- or alkyl-mercapto-alkyl or -alkoxy radicals by reaction with alkanols or alkylmercaptans.

Reactively esterified hydroxyl groups are here in particular hydroxyl groups esterified with the strong acids mentioned.

The reaction can be carried out in the usual manner, advantageously in the presence of solvents and, for example, in the presence of condensation agents, such as basic condensation agents, at lowered, ordinary or elevated temperature.

Furthermore, in compounds of the formula I wherein $R_1$ denotes an aryl radical substituted by a hydroxyl group, the hydroxyl group can be converted into a group of the formula $R_xO$—, wherein $R_x$ denotes an alkyl radical, an alkenyl radical, an alkinyl radical, an alkoxyalkyl radical or an alkylmercaptoalkyl radical. This conversion can be effected in the usual manner, for example by reaction with a reactive ester of an alcohol of the formula $R_xOH$ or a diazoalkane, such as diazomethane. Furthermore, hydroxyl groups in the radical Ph can be alkylated, for example by reaction with a reactive ester of a lower alkanol or a diazoalkane, such as diazomethane.

Reactive esters are above all esters with strong inorganic or organic acids, preferably with hydrogen halide acids, such as hydrochloric acid, hydrobromic acid or hydriodic acid, with sulphuric acid or with arylsulphonic acids, such as benzenesulphonic acid, p-bromobenzenesulphonic acid or p-toluenesulphonic acid.

The reaction can be carried out in the usual manner, advantageously in the presence of solvents. When using the reactive esters, the reaction is preferably carried out in the presence of condensation agents, such as basic condensation agents, or the phenolic hydroxy compound is employed in the form of a salt, for example a metal salt, such as an alkali metal salt, for example the sodium salt or potassium salt. The reaction can be carried out at lowered, ordinary or elevated temperature.

Furthermore it is possible, in compounds of the formula I, wherein $R_1$ denotes an aryl radical substituted by an amino group or by a substituent containing an amino group, and/or Ph denotes an o-phenylene radical containing an amino group, to acylate the said amino group or groups, such as, for example, by reaction with an acylating agent.

Possible acylating agents are carboxylic acids, for example aliphatic, araliphatic or cycloaliphatic carboxylic acids, preferably in the form of their functional derivatives, such as halides, especially chlorides, or anhydrides, for example pure or mixed anhydrides, or inner anhydrides, such as ketenes.

Furthermore, in compounds of the formula I which contain hydroxyl groups, these groups can be acylated (esterified). The acylation is carried out in the usual manner, for example by reaction with carboxylic acids, advantageously in the form of their reactive functional derivatives, such as acid halides, for example chlorides, esters, especially esters with lower alkanols, such as methanol and ethanol, or activated esters such as cyanomethyl esters, or pure or mixed anhydrides, for example mixed anhydrides with carbonic acid monoalkyl esters such as carbonic acid monoethyl ester and monoisobutyl ester.

In compounds of the formula I which contain an acylated hydroxyl or amino group, this group can be split in the usual manner to give the free hydroxyl or amino group respectively, and can in particular by split hydrolytically, with acid or basic catalysts as appropriate, for example with inorganic acids or alkali metal hydroxide solutions (bases), for example, with hydrochloric acid or with sodium hydroxide solution. If such splitting should already occur in the course of one of the above methods of manufacture, a resulting free hydroxyl or amino group can optionally be acylated as described above.

Furthermore, in compounds of the formula I which contain substituents with a C—C double bond or C—C triple bond, the C—C double bond or C—C triple bond can be converted into a C—C single bond by catalytic hydrogenation, such as by hydrogen in the presence of a hydrogenation catalyst, for example nickel, platinum or palladium, such as Raney nickel, platinum black or palladium on active charcoal. Care must be taken at the same time that other reducible groups are not attacked.

In compounds of the formula I, which contain substituents with a C—C triple bond, this bond can furthermore be reduced merely to a C—C double bond and can, if desired, be reduced stereospecifically to a C—C-cis- or C—C-trans-double bond. The reduction of a C—C triple bond to a C—C double bond can be carried out, for example, by hydrogenation with 1 mol of hydrogen in the presence of a less active hydrogenation catalyst, such as iron or palladium, for example Raney iron or palladium on barium sulphate, especially at elevated temperature. The reduction to a C—C-cis double bond can be effected, for example, by means of 1 mol of hydrogen in the presence of a deactivating catalyst, such as palladium on animal charcoal in the presence of quinoline, palladium on calcium carbonate in the presence of lead salts, or Raney nickel. The reduction to a C—C-trans-double bond can be effected, for example, by means of sodium in liquid ammonia, in which case, especially taking into account a urea group, short reaction times and no excess reducing agent are employed and, if appropriate, an ammonium halide, such as ammonium chloride, is added as the catalyst.

In resulting compounds of the formula I which contain an $\alpha$-aralkylamino or $\alpha$-aralkoxycarbonylamino group or an $\alpha$-aralkoxy or $\alpha$-aralkoxycarbonyloxy group, these radicals can be split to give free amino or hydroxyl groups respectively. $\alpha$-Aralkyl is in such cases especially benzyl. The splitting-off can be effected in the usual manner, especially by means of hydrogen in the presence of a hydrogenation catalyst, such as a palladium, platinum or nickel catalyst.

In resulting compounds of the formula I which possess nitro groups on an aromatic nucleus, these groups can be reduced to amino groups.

The reduction can be carried out in the usual manner, for example by nascent hydrogen (for example with iron and hydrochloric acid or with aluminium amalgam) or with catalytically activated hydrogen, such as hydrogen in the presence of platinum, nickel or palladium catalysts.

It is also possible to reduce compounds of the formula I, in which $R_3$ and $R_4$ together represent an oxo group, to compounds wherein $R_3$ represents hydroxyl and $R_4$ represents hydrogen.

The reduction of the oxo group is carried out in the usual manner, for example by metallic reduction, such as by treatment with sodium in alcohol, or with complex metal hydrides, such as sodium borohydride, or by means of catalytically activated hydrogen, for example hydrogen in the presence of a platinum, palladium, nickel or copper catalyst, such as platinum oxide, palladium on charcoal, Raney nickel or copper chromite. The reaction is preferably carried out in the presence of diluents and/or solvents, at low, ordinary or elevated temperature, in an open vessel or in a closed vessel, under pressure.

The reduction of the oxo group can also be carried out in accordance with the Meerwein-Ponndorf-Verley method. Thus, for example, the oxo compound can be treated in the usual manner with a lower alkanol, such as isopropanol, in the presence of a corresponding alkanolate, such as aluminium isopropylate.

It is also possible to oxidise compounds of the formula I, wherein $R_3$ represents hydroxyl and $R_4$ denotes hydrogen, to compounds in which $R_3$ and $R_4$ together denote an oxo group. Preferably, the starting compounds in that case are compounds in which $R_2$ denotes an acyloxy radical.

The oxidation is carried out in the usual manner, for example by treatment with oxidising agents, for example chromium-(VI) compounds, such as chromic acid or chromium trioxide/pyridine, hypohalites, such as tert. butyl hypochlorite, copper(II) salts, for example copper sulphate, or bismuth oxide, or, for example, by the Oppenauer method, for example by treatment with ketones, such as lower alkanones, for example acetone, cycloalkanones, such as cyclohexanone, or quinones in the presence of suitable catalysts, such as metal salts, especially aluminium salts, of branched lower alkanols, such as aluminium tert.-butylate or aluminum isopropylate, or aluminium phenolates; however, the oxidation can also be carried out with potassium permanganate, for exaple in acetone.

It is also possible to split off the hydroxyl group in compounds of the formula I, wherein $R_3$ represents hydroxyl. This gives compounds in which $R_3$ and $R_5$ represent a second bond.

The splitting off can be effected in the usual manner, for example by treatment with strong acids, such as sulphuric acid, p-toluenesulphonic acid, concentrated hydrochloric acid, oxalic acid or other dehydrating agents, such as phosphorus pentoxide, zinc chloride or boron trioxide. If appropriate, the water is removed by means of a water separator. For example, the reaction can be carried out in a boiling hydrocarbon, such as benzene or toluene.

Furthermore it is possible to replace the hydroxyl group by hydrogen in compounds of the formula I, wherein $R_3$ represents hydroxyl. This can be done, for example, by catalytic hydrogenation.

Furthermore, compounds of the formula I, wherein $R_3$ and $R_5$ represent a second bond, can be hydrogenated to compounds in which $R_3$ and $R_5$ represent hydrogen atoms. This can be done, in particular, by catalytic hydrogenation.

The catalytic hydrogenation can be carried out in the usual manner, in particular by means of hydrogen in the presence of a hydrogenation catalyst, such as a palladium, platinum or nickel catalyst.

The reactions mentioned can optionally be carried out simultaneously or successively, and in optional sequence.

The reactions mentioned can be carried out in the usual manner in the presence or absence of solvents or diluents, acid or basic condensation agents and/or catalysts, at lowered, ordinary or elevated temperature and if appropriate in a closed vessel under elevated pressure and/or under an inert gas atmosphere.

Depending on the process conditions and starting materials, the end products are obtained in the free form or in the form of their acid addition salts, which are also encompassed by the invention. Thus, for example, basic, neutral or mixed salts and at times also hemihydrates, monohydrates, sesquihydrates or polyhydrates thereof, can be obtained. The acid addition salts of the new compounds can be converted into the free compound in a manner which is in itself known, for example by means of basic agents, such as alkalis or ion exchangers. On the other hand, the resulting free bases can form salts with organic or inorganic acids. Acids used for the preparation of acid addition salts are especially those which are suitable for forming therapeutically usable salts. As examples of such acids there may be mentioned: hydrogen halide acids, for example hydrochloric acid, sulphuric acids, for example sulphuric acid, phosphoric acids, nitric acid, perchloric acid, aliphatic, alicyclic, aromatic or heterocyclic carboxylic acids or sulphonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid, fumaric acid, benzoic acid, p-aminobenzoic acid, anthranilic acid, p-hydroxybenzoic acid, salicylic acid or p-aminosalicylic acid, embonic acid, methanesulphonic acid, ethanesulphonic acid, hydroxyethanesulphonic acid, ethylenesulphonic acid; halogenobenzenesulphonic acid, toluenesulphonic acid, naphthalenesulphonic acid or sulphanilic acid; methionine, tryptophane, lysine or arginine.

These or other salts of the new compounds, such as, for example, the picrates, can also serve for the purification of the resulting free bases by converting the free bases into salts, isolating these and again liberating the bases from the salts. Because of the close relationships between the new compounds in the free form and in the form of their salts, the free compounds are, in the preceding and following text, where appropriate also to be understood as the corresponding salts, with regard to general sense and intended use.

The invention also relates to those embodiments of the process, according to which a compound obtainable as an intermediate product at any stage of the process is used as the starting material and the missing process steps are carried out, or the process is discontinued at any stage, or in which a starting material is formed under the reaction conditions or in which a reactant is present, if appropriate, in the form of an optical antipode and/or of a salt.

Thus, for example, the new piperidines can be obtained if a compound of the formula

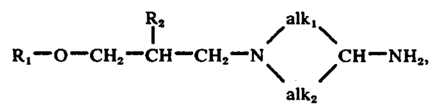

wherein $R_1$, $R_2$, $alk_1$ and $alk_2$ have the indicated meanings, is reacted with a compound of the formula

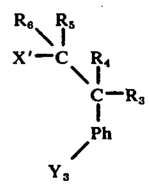

wherein $R_3$, $R_4$, $R_5$ and $R_6$ have the indicated meanings, and X' and $Y_3$ have the meanings indicated for formula VI or IX. Here, a product of the formula VI is produced as an intermediate and then reacts further, in accordance with the invention, to give a compound of the formula I. The reaction can be carried out in the usual manner, for example as described above for the intramolecular condensations.

The new compounds can, depending on the choice of the starting materials and procedures, be in the form of optical antipodes or reacemates or, if they contain at least two asymmetrical carbon atoms, also in the form of racemate mixtures and/or pure geometrical isomers or mixtures thereof (isomer mixtures).

Resulting isomer mixtures can be separated into the two pure geometrical isomers on the basis of the physico-chemical differences of the constituents in a known manner, for example by chromatography on a suitable stationary phase, such as silica gel, or aluminium oxide, which has been pretreated with a complex-forming heavy metal compound, for example with a silver compound, or by forming a heavy metal addition compound, for example the silver nitrate complex, separating this into the addition compounds of the pure isomers, for example by fractional crystallisation, and subsequently liberating the pure isomers.

Resulting pure isomers, for example trans-isomers, can be converted in the usual manner, for example photochemically, for example by irradiation with light of a suitable wavelength, advantageously in a suitable solvent, such as an aliphatic hydrocarbon, or in the presence of a suitable catalyst, into the isomers of opposite configuration, for example into the cis-isomers.

Racemate mixtures can be separated into the two stereoisomeric (diastereomeric) pure racemates on the basis of the physico-chemical differences of the constituents in a known manner, for example by chromatography and/or fractional crystallisation.

Resulting racemates can be resolved according to known methods, for example by recrystallisation from an optically active solvent, with the aid of micro-organisms or by reaction with an optically active acid which forms salts with the racemic compound and separation of the salts obtained in this manner, for example on the basis of their different solubilities, into the diastereomers, from which the antipodes can be liberated by treatment with suitable agents. Particularly customary optically active acids are, for example, the D- and L-forms of tartaric acid, di-o-toluyltartaric acid, malic acid, mandelic acid, camphorsulphonic acid or quinic acid. Advantageously, the more active L-antipode is isolated.

Suitably, those starting materials are used for carrying out the reactions according to the invention which lead to the initially particularly mentioned groups of end products and particularly to the end products which have been specifically described or singled out.

The starting materials are known or can, if they are new, be obtained according to methods which are in themselves known.

The compounds of the formula

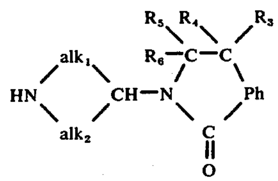
(IIIa)

used as preferred starting materials, can be obtained, for example, if a compound of the formula

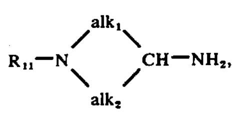

wherein $alk_1$ and $alk_2$ have the indicated meanings and $R_{11}$ denotes an $\alpha$-aralkyl radical, such as a benzyl radical, is reacted with a compound of the formula

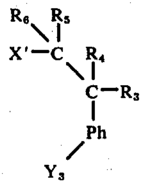

wherein $R_3$, $R_4$, $R_5$ and $R_6$ have the indicated meanings and X' and $Y_3$ have the meanings indicated for formulae VI or IX, and in the resulting compound of the formula

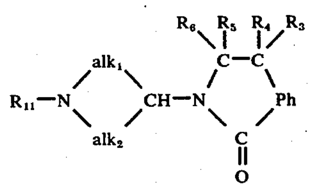

the $\alpha$-aralkyl radical $R_{11}$ is replaced by hydrogen, for example by catalytic hydrogenation as described above.

The new compounds can be used as medicaments, for example in the form of pharmaceutical preparations in which they or their salts are present in a mixture with a pharmaceutical, organic or inorganic, solid or liquid excipient which is suitable, for example, for enteral, for example oral, or parenteral administration. Suitable materials for forming the excipient are those which do not react with the new compounds such as, for example, water, gelatine, lactose, starch, magnesium stearate, talc, vegetable oils, benzyl alcohols, gum, polyalkylene glycols, white petroleum jelly, cholesterol or other known medicinal excipients. The pharmaceutical preparations can be, for example, in the form of tablets, dragees, capsules, suppositories, ointments or creams or in a liquid form, as solutions (for example as an elixir or syrup), suspensions or emulsions. They are optionally sterilised and/or contain auxiliaries, such as preservatives, stabilisers, wetting agents or emulsifiers, salts for regulating the osmotic pressure or buffers. They can also contain yet other therapeutically valuable materials. The preparations, which can also be used in veterinary medicine, are formulated according to customary methods.

The dosage of the new compounds depends on the nature of the conditions to be treated and on the individual requirements. For example, the new compounds can be administered to a warm-blooded animal of about 75 kg body weight in a daily dose of about 5–100 mg, especially about 5 to 60 mg.

The new compounds can also be used advantageously in pharmaceutical preparations in combination with other antihypertensive agents and/or diuretics.

Compounds, having an anti-hypertensive action, which can be used are in particular those of the type of $\alpha$-amino-$\beta$-hydroxyphenyl-propionic acid and $\beta$-amino-$\beta$-alkoxyphenylpropionic acid and especially of the hydrazinopyridazines and of the sympathicolytics.

Suitable diuretics are materials which increase the diuresis both through renal and through extrarenal action on the tissues. For this purpose, substances with an inhibiting action on the back-resorption in the tubulus, such as, for example, in particular saluretics as well as ethacrinic acid and its analogues, can be used.

Particularly suitable compounds are benzothiadiazine derivatives, such as thiazides and hydrothiazides, benzene-sulphonamides, phenoxyacetic acids, benzofurane-2-carboxylic acids and benzofurane-2,3-dihydroxy-2-carboxylic acids.

The examples which follow illustrate the invention without however restricting it.

EXAMPLE 1

A mixture of 30.2 g of 1-(o-methoxyphenoxy)-2,3-epoxypropane and 38.7 g of 2-(4-piperidyl)-3,4-dihydro-1(2H)-isoquinolinone in 50 ml of absolute ethanol is boiled for 6 hours under reflux and is then evaporated in vacuo. The residue is acidified with ethanolic hydrochloric acid; on adding ether, 2-{1-[3-(o-methoxyphenoxy)-2-hydroxypropyl]-4-piperidyl}-3,4-dihydro-1(2H)-isoquinolinone hydrochloride precipitates and after recrystallisation from ethanol/ether melts at 174°–176° C.

2-(4-Piperidyl)-3,4-dihydro-1(2H)-isoquinolinone, used as the starting material, is prepared as follows:

A solution of 40 g of 2-(2-chloroethyl)-benzoyl chloride in 100 ml of acetone is added dropwise to a mixture of 53 g of potassium hydroxide and 30 g of 4-amino-1-benzyl-piperidine in 600 ml of acetone at room temperature. After completion of the addition, the reaction mixture is heated for 4 hours to the reflux temperature and is then evaporated to dryness. The residue is taken up in water and extracted with methylene chloride. The organic layer is dried over sodium sulphate and evaporated. The oily residue is taken up in a little ethanol and acidified with ethanolic hydrochloric acid. The hydrochloride of 2-(1-benzyl-4-piperidyl)-3,4-dihydro-1(2H)-isoquinolinone is obtained in a crystalline form and melts at 276°–278° C (with decomposition).

13.6 g of 2-(1-benzyl-4-piperidyl)-3,4-dihydro-1(2H)-isoquinolinone hydrochloride are hydrogenated together with 1.5 g of 10% strength palladium on charcoal at room temperature and atmospheric pressure. The reaction mixture is freed from the catalyst by filtration and the residue is well washed with water. The filtrate is evaporated to dryness, the residue is dissolved in as little ethanol as possible and the hydrochloride of 2-(4-piperidyl)-3,4-dihydro-1(2H)-isoquinolinone is precipitated with ether. It melts, after recrystallisation from ethanol, at 318°–320° C (decomposition).

The base is liberated with 10 N sodium hydroxide solution and extracted with methylene chloride. Drying, and evaporation of the solvent, gives the base as an oil.

EXAMPLE 2

A solution of 9.9 g (0.06 mol) of 1-(o-tolyloxy)-2,3-epoxy-propane, 15.9 g (0.06 mol) of 2-(4-piperidyl)-3,4-dihydro-1-(2H)-isoquinolinone hydrochloride and 24 ml of triethylamine in 240 ml of isopropanol is heated to the reflux temperature for 6 hours and then evaporated in vacuo. The residue is crystallised from ethanol-water. After recrystallisation from ethanol-water, 2-{1-[3-(o-tolyloxy)-2-hydroxypropyl]-4-piperidyl}-3,4-dihydro-1(2H)-isoquinolinone melts at 104°–105° C.

The maleic acid salt of this compound melts, after recrystallisation from ethanol-ether, at 165°–166° C (with decomposition).

EXAMPLE 3

A solution of 8.1 g of 2-{1-[3-(o-methoxy-phenoxy)-2-hydroxy-1-propyl]-piperidyl-(4)}-3,4-dihydro-1-(2H)-isoquinolinone hydrochloride and 5 g of pivaloyl chloride in 50 ml of pyridine is warmed to 100° C over the course of ½ hour and is then evaporated in vacuo. The residue is acidified with alcoholic hydrochloric acid and again evaporated. After recrystallisation from isopropanol, 2-{-[3-(o-methoxyphenoxy)-2-pivaloyloxy-1-propyl]-piperidyl-(4)}-3,4-dihydro1-(2H)-isoquinolinone hydrochloride of melting point 232°–234° C is obtained.

EXAMPLE 4

A mixture of 5.5 g of 1-(o-chlorophenoxy)-2,3-epoxypropane and 7 g of 2-(4-piperidyl)-3,4-dihydro-1(2H)-isoquinolinone in 100 ml of isopropanol is boiled for 5 hours under reflux and then evaporated in vacuo. The oily residue is dissolved in absolute ethanol and the equivalent amount of maleic acid is added. After addition of ether, 2-{1-([3-(o-chlorophenoxy)-2-hydroxy-propyl]-piperidyl-(4)}-3,4-dihydro-1(2H)-isoquinolinone maleate precipitates, and melts, after recrystallisation from ethanol/ether at 139°–140° C.

EXAMPLE 5

Tablets containing 2-{1-[3-(o-methoxyphenoxy)-2-hydroxypropyl]-4-piperidyl}-3,4-dihydro-1-(2H)-isoquinolone.

COMPOSITION

2-{1-[3-(o-Methoxyphenoxy)-2-hydroxypropyl]-4-piperidyl}-3,4-dihydro-1-(2H)-isoquinolone
Crystalline lactose
Wheat starch
Aerosil 200
Talc
Magnesium stearate

EXAMPLE 6

A solution of 6.2 g of 1-[p-(2-methoxy-ethyl)-phenoxy]-2,3-epoxy-propane and 7.0 g of 2-(4-piperidyl)-3,4-dihydro-1(2H)-isoquinolinone in 80 ml of isopropanol is refluxed for 5 hours. The reaction mixture is concentrated by evaporation to dryness with the resulting precipitation of 2-{1-[3-<p-(2-methoxy-ethyl)-phenoxy>-2-hydroxypropyl]-4-piperidyl}-3,4-dihydro-1(2H)-isoquinolinone. The product melts at 116°–117° after recrystallisation from an ethanol/ether mixture. The maleic acid salt crystallises from a mixture of ethanol/ether and melts at 138°–139°.

EXAMPLE 7

6.1 g of 1-(o-allyloxyphenoxy)-2,3-epoxy-propane and 7.0 g of 2-(4-piperidyl)-3,4-dihydro-1(2H)-isoquinoline are dissolved in 100 ml of isopropanol. The solution is refluxed for 5 hours and then concentrated in vacuo. The oily residue is converted with 3.1 g of fumaric acid into the crystalline 2-{1-[3-(o-allyloxyphenoxy)-2-hydroxypropyl]-4-piperidyl}-3,4-dihydro-1(2H)-isoquinolinone-fumarate. The salt melts at 145°–146° after recrystallisation from ethanol/ether, with decomposition.

EXAMPLE 8

A mixture of 28 g of 1-($\beta$-naphthoxy)-2,3-epoxy-propane and 18.8 g of 2-(4-piperidyl)-3,4-dihydro-1(2H)-isoquinolinone in 40 ml of isopropanol is refluxed for 4 hours. After completion of the reaction, the precipitated crystals are filtered off and washed with ether. There is thus obtained 2-{1-[3-($\beta$-naphthoxy)-2-hydroxy-1-propyl]-piperidyl-(4)}-3,4-dihydro-1(2H)-isoquinolinone, which melts at 181°–183° after recrystallisation from chloroform/ethanol.

24 g of the above base is dissolved in 250 ml of hot chloroform, and 30 ml of 2N ethanolic hydrochloric acid is added to the solution. There precipitates the hydrochloride of 2-{1-[3-($\beta$-naphthoxy)-2-hydroxy-1-propyl]-piperidyl-(4)}-3,4-dihydro-1(2H)-isoquinolinone, which melts at 269°–271°.

EXAMPLE 9

A mixture of 26.9 g of 1-(2-methoxy-4-chlorophenoxy)-2,3-epoxy-propane and 25.8 g of 2-(4-piperidyl)-3,4-dihydro-1(2H)-isoquinolinone in 30 ml of isopropanol is refluxed for 4 hours. After completed reaction, trituration with ether is performed, whereupon 2-{1-[3-(2-methoxy-4-chlorophenoxy)-2-hydroxy-1-propyl]-piperidyl-(4)}-3,4-dihydro-1(2H)-isoquinolinone precipitates, which melts at 108°–110° after recrystallisation from isopropanol.

22.8 g of the above base is dissolved in 60 ml of hot isopropanol, and to this solution there is added 10 ml of 8.7N ethanolic hydrochloric acid. After trituration with ether there precipitates the hydrochloride of 2-{1-[3-(2-methoxy-4-chlorophenoxy)-2-hydroxy)-1-propyl]-piperidyl-(4)}-3,4-dihydro-1(2H)-isoquinolinone, which melts at 210°–212°.

EXAMPLE 10

A mixture of 11.55 g of 1-(o-cyanophenoxy)-2,3-epoxy-propane and 14.95 g of 2-(4-piperidyl)-3,4-dihydro-1(2H)-isoquinolinone in 30 ml of isopropanol is refluxed for 6 hours. After completion of the reaction, the reaction solution is diluted with 150 ml of isopropanol, heated to boiling and filtered hot. On cooling and with trituration with ether there precipitates 2-{1-[3-(o-cyanophenoxy)-2-hydroxy-1-propyl]-piperidyl-(4)}-3,4-dihydro-1(2H)-isoquinolinone, which melts at 138°–140°.

16.5 g of the above base is dissolved in 100 ml of hot ethanol, and 5 g of maleic acid is added. On cooling of the solution there precipitates the maleate of 2-{1-[3-(o-cyanophenoxy)-2-hydroxy-1-propyl]-piperidyl-(4)}-3,4-dihydro-1-(2H)-isoquinolinone, which melts at 183°–184°.

EXAMPLE 11

A mixture of 18 g of 1-(o-methoxyphenoxy)-2,3-epoxy-propane, 27 g of 4-phthalimidopiperidine-hydrochloride, 60 ml of triethylamine and 300 ml of isopropanol is refluxed for 4 hours. The reaction mixture is concentrated by evaporation to dryness, and the residue is suspended in 2N sodium hydroxide solution. The aqueous suspension is extracted with methylene chloride, the organic phase is dried with sodium sulphate and freed from the solvent in vacuo. 11.6 g of maleic acid is added to the residue. The maleic acid salt of 1-[3-(o-methoxyphenoxy)-2-hydroxypropyl]-4-phthalimidopiperidine is crystallised from ethanol/ether and melts at 201°–202° with decomposition.

MANUFACTURE

The active compound is mixed with a part of the wheat starch, with lactose and with Aerosil 200 and the mixture is forced through a sieve. A further part of the wheat starch is worked into a paste with a 5-fold amount of water on a waterbath and the powder mixture is kneaded with this paste until a slightly plastic mass has been produced. The plastic mass is pressed through a sieve of approx. 3 mm mesh width and dried, and the dried granules are again forced through a sieve. Thereafter, the remaining wheat starch, talc and magnesium stearate are mixed in and the resulting mixture is pressed to give tablets having a cross-shaped notch.

We claim:

1. A 1-(3-aryloxy-2-hydroxy- or 2-alkanoyloxy-propyl)-4-(1-oxoisoquinolino)-piperidine compound corresponding to formula

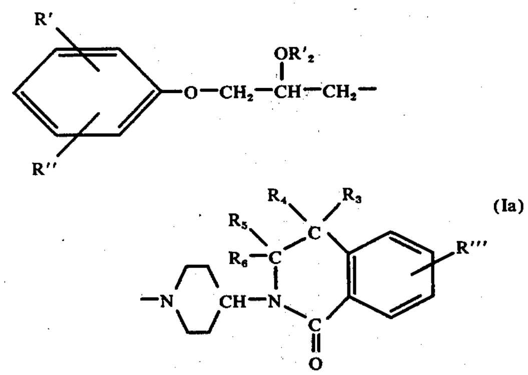

wherein R' and R'' are hydrogen, lower o-alkyl, lower o-alkenyl, lower o-alkoxy, lower o-alkenyloxy or an o-halogen atom and R' and R'' together with the phenyl radical form a $\beta$-naphthyl radical, $R_2'$ denotes hydrogen or lower alkanoyl, $R_3$ denotes hydrogen, $R_4$, $R_5$ and $R_6$ denote hydrogen, R''' denotes hydrogen, lower alkyl, lower alkoxy, halogen, or trifluoromethyl, or a therapeutically useful acid addition salt thereof, wherein said open chain groups have up to 4 carbon atoms.

2. A compound as claimed in claim 1, corresponding to formula Ia, wherein R' denotes lower o-alkenyl, lower o-alkenyloxy, lower o-alkyl, or lower o-alkoxy, R'' represents hydrogen, $R_2'$ denotes acetyl, propionyl, pivaloyl, or hydrogen, $R_3$ denotes a hydrogen, and $R_4$, $R_5$, $R_6$ and R''' each denote hydrogen or a therapeutically useful acid addition salt thereof.

3. A compound as claimed in claim 1, corresponding to formula Ia, wherein R' denotes o-allyl, o-allyloxy, o-methyl or o-methoxy, R'' represents hydrogen, $R_2'$ denotes the acetyl, propionyl, pivaloyl, or hydrogen, $R_3$ denotes a hydrogen, and $R_4$, $R_5$, $R_6$ and R''' denote hydrogen, or a therapeutically useful acid addition salt thereof.

4. A compound as claimed in claim 1 and being 2-{1-[3-(o-Allyloxyphenoxy)-2-hydroxypropyl]-4-piperidyl}-3,4-dihydro-1(2H)-isoquinolinone and a therapeutically useful acid addition salt thereof.

5. A compound as claimed in claim 1 and being 2-{1-[3-(o-chlorophenoxy)-2-hydroxypropyl]-4-piperidyl}-3,4-dihydro-1(2H)-isoquinolinone and a therapeutically useful acid addition salt thereof.

6. A compound as claimed in claim 1 and being 2-{1-[3-(o-methoxyphenoxy)-2-pivaloyloxy-propyl]-4-piperidyl}-3,4-dihydro-1(2H)-isoquinolinone and a therapeutically useful acid addition salt thereof.

7. A compound as claimed in claim 1 and being 2-{1-[3-(o-Tolyloxy)-2-hydroxypropyl]-4-piperidyl}-3,4- dihydro-1(2H)-isoquinolinone and a therapeutically useful acid addition salt thereof.

8. A compound as claimed in claim 1 and being 2-{1-[3-(o-methoxyphenoxy)-2-hydroxypropyl]-4-piperidyl}-3,4-dihydro-1(2H)-isoquinolinone and a therapeutically useful acid addition salt thereof.

9. An antihypertensive pharmaceutical composition comprising a therapeutically effective amount of a compound claimed in claim 1, together with a pharmaceutical excipient.

* * * * *